US012109382B2

(12) United States Patent
Wen (10) Patent No.: US 12,109,382 B2
(45) Date of Patent: Oct. 8, 2024

(54) DEVICE SET DESIGNED FOR PCNL SURGERY

(71) Applicant: BECTON, DICKINSON AND COMPANY, Franklin Lakes, NJ (US)

(72) Inventor: Xin Wen, Shanghai (CN)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 658 days.

(21) Appl. No.: 17/000,289

(22) Filed: Aug. 22, 2020

(65) Prior Publication Data

US 2021/0052876 A1   Feb. 25, 2021

(30) Foreign Application Priority Data

Aug. 23, 2019   (CN) .......................... 201910783544.2

(51) Int. Cl.
*A61M 39/02*   (2006.01)
*A61B 17/34*   (2006.01)
(Continued)

(52) U.S. Cl.
CPC ......... *A61M 39/0247* (2013.01); *A61B 17/34* (2013.01); *A61B 50/30* (2016.02); *A61M 1/69* (2021.05); *A61M 25/02* (2013.01); *A61M 25/09* (2013.01); *A61M 25/10* (2013.01); *A61M 29/00* (2013.01); *A61M 39/22* (2013.01);
(Continued)

(58) Field of Classification Search
CPC .. A61M 39/0247; A61M 25/02; A61M 25/09; A61M 25/10; A61M 29/00; A61M 39/22; A61M 2039/229; A61B 50/30; A61B 17/34; A61B 17/3415; A61B 17/3417; A61B 17/3421;
(Continued)

(56) References Cited

U.S. PATENT DOCUMENTS

| 4,552,554 | A | * | 11/1985 | Gould | .................... | A61M 25/01 |
| | | | | | | 604/164.13 |
| 4,950,257 | A | * | 8/1990 | Hibbs | ............... | A61M 39/0606 |
| | | | | | | 604/167.04 |

(Continued)

FOREIGN PATENT DOCUMENTS

| CN | 201379888 Y | * | 1/2010 |
| CN | 204485018 U | * | 7/2015 |

(Continued)

OTHER PUBLICATIONS

CN 204485018 English Translation (Year: 2015).*
CN206434630 U English Translation (Year: 2017).*

*Primary Examiner* — Katherine H Schwiker
*Assistant Examiner* — Zehra Jaffri
(74) *Attorney, Agent, or Firm* — Dickinson Wright PLLC; Andrew D. Dorisio (57) ABSTRACT

A device set designed for PCNL surgery includes a puncture needle, a guidewire, a dilator, a balloon catheter, a sheath, and a drainage catheter which are all placed in a single package. A tip length of the dilator is substantially the same as a tip length of the balloon catheter. The device set may include a puncture needle, a guidewire, a plurality of dilators having different sizes, a sheath, and a drainage catheter, which are all placed in a single package, wherein all the dilators have substantially the same tip length.

10 Claims, 4 Drawing Sheets

(51) Int. Cl.
*A61B 50/30* (2016.01)
*A61M 1/00* (2006.01)
*A61M 25/00* (2006.01)
*A61M 25/02* (2006.01)
*A61M 25/09* (2006.01)
*A61M 25/10* (2013.01)
*A61M 29/00* (2006.01)
*A61M 39/22* (2006.01)

(52) U.S. Cl.
CPC ............... *A61B 2017/3413* (2013.01); *A61B 2050/3008* (2016.02); *A61M 1/84* (2021.05); *A61M 25/002* (2013.01); *A61M 2039/229* (2013.01)

(58) Field of Classification Search
CPC .. A61B 2017/3433; A61B 2017/22051; A61B 2017/22072; A61B 2017/22074
See application file for complete search history.

(56) References Cited

U.S. PATENT DOCUMENTS

| | | | |
|---|---|---|---|
| 6,010,520 A * | 1/2000 | Pattison | A61M 29/00 606/191 |
| 6,171,248 B1 | 1/2001 | Hossack et al. | |
| 6,190,915 B1 | 2/2001 | Madsen et al. | |
| 6,238,343 B1 | 5/2001 | Madsen et al. | |
| 6,368,277 B1 | 4/2002 | Mao | |
| 6,494,860 B2 * | 12/2002 | Rocamora | A61M 25/0668 604/161 |
| 6,520,934 B1 | 2/2003 | Lee et al. | |
| 6,540,721 B1 | 4/2003 | Voyles | |
| 6,589,262 B1 | 7/2003 | Honebrink | |
| 6,599,237 B1 | 7/2003 | Singh | |
| 6,605,943 B1 | 8/2003 | Clark | |
| 6,647,132 B1 | 11/2003 | Montillo | |
| 6,663,595 B2 | 12/2003 | Spohn | |
| 6,673,060 B1 | 1/2004 | Fleming, III | |
| 6,692,464 B2 | 2/2004 | Graf | |
| 6,723,052 B2 | 4/2004 | Mills | |
| 6,733,489 B2 | 4/2004 | Nutting | |
| 6,736,803 B2 | 5/2004 | Cawood | |
| 6,796,991 B2 | 5/2004 | Nardeo | |
| 6,748,973 B2 | 6/2004 | Lindroos | |
| 6,892,087 B2 | 5/2005 | Osypka | |
| 6,905,458 B2 | 6/2005 | Choay et al. | |
| 6,939,370 B2 | 9/2005 | Hartley | |
| 7,001,369 B2 | 2/2006 | Griffin et al. | |
| 7,001,396 B2 | 2/2006 | Glazier et al. | |
| 7,048,717 B1 | 5/2006 | Frassica | |
| 7,101,353 B2 | 9/2006 | Lui et al. | |
| 7,104,979 B2 | 9/2006 | Jansen et al. | |
| 7,153,277 B2 | 12/2006 | Skujins et al. | |
| 7,158,692 B2 | 1/2007 | Chalana et al. | |
| 7,217,256 B2 | 5/2007 | Di Palma | |
| 7,258,669 B2 | 8/2007 | Russell | |
| 7,276,062 B2 | 10/2007 | McDaniel et al. | |
| 7,306,585 B2 | 12/2007 | Ross | |
| 7,314,481 B2 | 1/2008 | Karpiel | |
| 7,322,959 B2 | 1/2008 | Warnack et al. | |
| 7,462,488 B2 | 12/2008 | Madsen et al. | |
| 7,481,805 B2 | 1/2009 | Magnusson | |
| 7,510,568 B2 | 3/2009 | Bleam et al. | |
| 7,524,305 B2 | 4/2009 | Moyer | |
| 7,534,250 B2 | 5/2009 | Schaeffer et al. | |
| 7,578,814 B2 | 8/2009 | Accisano, III et al. | |
| 7,591,813 B2 | 9/2009 | Levine et al. | |
| 7,655,021 B2 | 2/2010 | Brasington et al. | |
| 7,677,078 B2 | 3/2010 | Sauer et al. | |
| 7,678,100 B2 | 3/2010 | Chin et al. | |
| 7,704,245 B2 | 4/2010 | Dittman et al. | |
| 7,722,567 B2 | 5/2010 | Tal | |
| 7,736,331 B2 | 6/2010 | Accisano, III et al. | |
| 7,780,715 B2 | 8/2010 | Shaked et al. | |
| 7,794,402 B2 | 9/2010 | Wang | |
| 7,833,597 B2 | 11/2010 | Bavaro et al. | |
| 7,857,820 B2 | 12/2010 | Skakoon et al. | |
| 7,874,987 B2 | 1/2011 | Altmann et al. | |
| 7,875,021 B2 | 1/2011 | Minassians | |
| 7,879,024 B2 | 2/2011 | Thorstenson et al. | |
| 7,909,798 B2 | 3/2011 | Osypka | |
| 7,909,814 B2 | 3/2011 | Accisano, III et al. | |
| 7,922,696 B2 * | 4/2011 | Tal | A61B 17/3496 604/165.01 |
| 7,951,093 B2 | 5/2011 | Skujins et al. | |
| 7,961,929 B2 | 6/2011 | Ni et al. | |
| 7,968,038 B2 | 6/2011 | Dittman et al. | |
| 7,985,232 B2 | 7/2011 | Potter et al. | |
| 7,993,272 B2 | 8/2011 | Chomas et al. | |
| 7,993,305 B2 | 8/2011 | Ye et al. | |
| 8,070,694 B2 | 12/2011 | Galdonik et al. | |
| 8,105,287 B2 | 1/2012 | Fisher et al. | |
| 8,137,309 B2 | 3/2012 | Nishtala et al. | |
| 8,137,317 B2 | 3/2012 | Osypka | |
| 8,147,452 B2 | 4/2012 | Nardeo et al. | |
| 8,147,456 B2 | 4/2012 | Fisher et al. | |
| 8,157,790 B2 | 4/2012 | Kubo et al. | |
| 8,177,770 B2 | 5/2012 | Rasmussen et al. | |
| 8,262,671 B2 | 9/2012 | Osypka | |
| 8,273,059 B2 | 9/2012 | Nardeo et al. | |
| 8,287,585 B2 | 10/2012 | Gurm | |
| 8,292,852 B2 | 10/2012 | Mulholland et al. | |
| 8,366,674 B2 | 2/2013 | Frassica et al. | |
| 8,377,083 B2 | 2/2013 | Mauch et al. | |
| 8,460,323 B2 | 6/2013 | Mauch et al. | |
| 8,478,383 B2 | 7/2013 | Bar-Tal et al. | |
| 8,500,688 B2 | 8/2013 | Engel et al. | |
| 8,517,993 B2 | 8/2013 | Freas et al. | |
| 8,591,567 B2 | 11/2013 | Chau et al. | |
| 8,639,310 B2 | 1/2014 | Chen et al. | |
| 8,652,098 B2 | 2/2014 | Haslinger | |
| 8,696,582 B2 | 4/2014 | Rohling | |
| 8,700,129 B2 | 4/2014 | Hauck et al. | |
| 8,734,426 B2 | 5/2014 | Ahmed et al. | |
| 8,753,313 B2 | 6/2014 | Kimmel et al. | |
| 8,771,225 B2 | 7/2014 | Ahn | |
| 8,795,311 B2 | 8/2014 | Griffith et al. | |
| 8,827,958 B2 | 9/2014 | Bierman et al. | |
| 8,834,499 B2 | 9/2014 | Mauch et al. | |
| 8,845,614 B2 | 9/2014 | Raabe et al. | |
| 8,888,787 B2 | 11/2014 | Wynberg | |
| 8,906,268 B2 | 12/2014 | Boutet et al. | |
| 8,911,400 B2 | 12/2014 | Ferry | |
| 8,926,560 B2 | 1/2015 | Dinh et al. | |
| 8,948,474 B2 | 2/2015 | Chang et al. | |
| 8,986,283 B2 | 3/2015 | Rajendran et al. | |
| 8,998,814 B2 | 4/2015 | Oikawa et al. | |
| 9,044,266 B2 | 6/2015 | Nimgaard | |
| 9,044,577 B2 | 6/2015 | Bishop et al. | |
| 9,060,756 B2 | 6/2015 | Bencini et al. | |
| 9,089,672 B2 | 7/2015 | Hendriksen et al. | |
| 9,126,019 B2 | 9/2015 | Guo et al. | |
| 9,149,176 B2 | 10/2015 | Greenberg et al. | |
| 9,149,606 B2 | 10/2015 | Beissel et al. | |
| 9,174,036 B2 | 11/2015 | Okamura et al. | |
| 9,186,484 B2 | 11/2015 | Defossez et al. | |
| 9,233,226 B2 | 1/2016 | Lampropoulos et al. | |
| 9,241,735 B2 | 1/2016 | Nishtala et al. | |
| 9,242,076 B2 | 1/2016 | Burton et al. | |
| 9,248,261 B2 | 2/2016 | Schweikert et al. | |
| 9,254,146 B2 | 2/2016 | Massengale et al. | |
| 9,282,945 B2 | 3/2016 | Smith et al. | |
| 9,314,749 B2 | 4/2016 | Yagi et al. | |
| 9,352,132 B2 | 5/2016 | Urie | |
| 9,393,041 B2 | 7/2016 | Barker et al. | |
| 9,398,936 B2 | 7/2016 | Razzaque et al. | |
| 9,409,001 B2 | 8/2016 | Aggerholm et al. | |
| 9,420,992 B2 | 8/2016 | Sheldon et al. | |
| 9,445,837 B2 | 9/2016 | Fulton, III | |
| 9,474,882 B2 | 10/2016 | Franklin | |
| 9,492,638 B2 | 11/2016 | McKinnis et al. | |
| 9,498,282 B2 | 11/2016 | Fernald | |
| 9,504,476 B2 * | 11/2016 | Gulachenski | A61M 25/10 |

(56) References Cited

U.S. PATENT DOCUMENTS

| | | |
|---|---|---|
| 9,517,185 B1 | 12/2016 | Al-Jazaeri |
| 9,522,253 B2 | 12/2016 | Gandras et al. |
| 9,538,981 B2 | 1/2017 | Rioux et al. |
| 9,539,415 B2 | 1/2017 | Racz et al. |
| 9,545,506 B2 | 1/2017 | Quigley |
| 9,566,087 B2 | 2/2017 | Bierman et al. |
| 9,566,413 B2 | 2/2017 | Eberhardt et al. |
| 9,629,981 B2 | 4/2017 | Thungana et al. |
| 9,655,594 B2 | 5/2017 | Oraevsky et al. |
| 9,668,654 B2 | 6/2017 | Rajendran et al. |
| 9,693,820 B2 | 7/2017 | Potter et al. |
| 9,706,988 B2 | 7/2017 | Nobles et al. |
| 9,717,884 B2 | 8/2017 | Matsumoto et al. |
| 9,737,284 B2 | 8/2017 | Kim et al. |
| 9,764,111 B2 | 9/2017 | Gulachenski |
| 9,764,117 B2 * | 9/2017 | Bierman .......... A61M 25/0612 |
| 9,773,307 B2 | 9/2017 | Chang et al. |
| 9,839,770 B2 | 12/2017 | Linden et al. |
| 9,861,385 B2 | 1/2018 | Fulton |
| 9,872,666 B2 | 1/2018 | Quearry |
| 9,877,704 B2 | 1/2018 | Ogawa |
| 9,884,169 B2 | 2/2018 | Bierman et al. |
| 9,920,188 B2 | 3/2018 | Vogt et al. |
| 9,950,158 B2 | 4/2018 | True et al. |
| 9,955,940 B1 | 5/2018 | Coats et al. |
| 9,972,082 B2 | 5/2018 | Holsing et al. |
| 9,980,699 B2 | 5/2018 | Quearry et al. |
| 10,004,475 B2 | 6/2018 | Quearry |
| 10,010,701 B2 | 7/2018 | Ahmed et al. |
| 10,034,655 B2 | 7/2018 | McKinnis et al. |
| 10,074,037 B2 | 9/2018 | Lu et al. |
| 10,076,307 B2 | 9/2018 | Coats et al. |
| 10,080,873 B2 | 9/2018 | Stapleton et al. |
| 10,086,174 B2 | 10/2018 | Crall et al. |
| 10,111,645 B2 | 10/2018 | Fearnot et al. |
| 10,118,027 B2 | 11/2018 | Seifert et al. |
| 10,137,020 B2 | 11/2018 | Treacy et al. |
| 10,143,455 B2 | 12/2018 | Lichty, II et al. |
| 10,166,070 B2 | 1/2019 | Davies et al. |
| 10,169,641 B2 | 1/2019 | Lee et al. |
| 10,173,033 B2 | 1/2019 | Leung et al. |
| 10,182,804 B2 | 1/2019 | Walters et al. |
| 10,183,147 B2 | 1/2019 | Yang et al. |
| 10,188,371 B2 | 1/2019 | Madsen et al. |
| 10,213,582 B2 | 2/2019 | Garrison et al. |
| 10,213,583 B2 | 2/2019 | Klocke et al. |
| 10,219,788 B2 | 3/2019 | Tabeie |
| 10,220,192 B2 | 3/2019 | Drasler et al. |
| 10,226,203 B2 | 3/2019 | Stigall et al. |
| 10,226,264 B2 | 3/2019 | McIntosh et al. |
| 10,238,463 B2 | 3/2019 | Verstege et al. |
| 10,238,834 B2 | 3/2019 | Bridgeman et al. |
| 10,249,037 B2 | 4/2019 | Chang et al. |
| 10,252,028 B2 | 4/2019 | Katsurada et al. |
| 10,265,234 B1 * | 4/2019 | Zwierstra .......... A61B 8/40 |
| 11,529,522 B2 * | 12/2022 | Bornzin .......... A61N 1/0573 |
| 2002/0198492 A1 * | 12/2002 | Miller .......... A61M 25/1027 |
| | | 604/96.01 |
| 2008/0132933 A1 | 6/2008 | Gerber |
| 2008/0154206 A1 * | 6/2008 | Guo .......... A61M 25/0668 |
| | | 604/164.05 |
| 2009/0030370 A1 | 1/2009 | Nishtala et al. |
| 2010/0010530 A1 * | 1/2010 | Rhee .......... A61F 2/26 |
| | | 606/192 |
| 2011/0054381 A1 * | 3/2011 | Van Dam .......... A61B 17/1114 |
| | | 606/108 |
| 2011/0181614 A1 | 7/2011 | Chang et al. |
| 2011/0224538 A1 | 9/2011 | Linares |
| 2013/0103004 A1 | 4/2013 | Gray et al. |
| 2013/0190609 A1 | 7/2013 | Fischer, Jr. |
| 2013/0226094 A1 | 8/2013 | Ahmed et al. |
| 2014/0180068 A1 | 6/2014 | Spencer et al. |
| 2014/0206987 A1 | 7/2014 | Urbanski et al. |
| 2014/0221828 A1 | 8/2014 | McKinnis et al. |
| 2014/0257090 A1 | 9/2014 | Fischer, Jr. et al. |
| 2014/0265024 A1 | 9/2014 | Quearry |
| 2014/0276073 A1 | 9/2014 | Quearry |
| 2015/0086094 A1 | 3/2015 | Chang et al. |
| 2015/0086095 A1 | 3/2015 | Chang et al. |
| 2015/0112256 A1 | 4/2015 | Byrne et al. |
| 2015/0150586 A1 | 6/2015 | Aggerholm et al. |
| 2015/0272542 A1 | 10/2015 | Shuman et al. |
| 2015/0273120 A1 | 10/2015 | Zamarripa et al. |
| 2015/0320979 A1 | 11/2015 | Fearnot et al. |
| 2016/0120509 A1 | 5/2016 | Syed et al. |
| 2016/0128718 A1 | 5/2016 | Aggerholm et al. |
| 2016/0193448 A1 | 7/2016 | Nardeo et al. |
| 2016/0223308 A1 | 8/2016 | Rhee et al. |
| 2016/0331929 A1 | 11/2016 | Lampropoulos et al. |
| 2017/0021139 A1 | 1/2017 | Bajema et al. |
| 2017/0032557 A1 | 2/2017 | Anand et al. |
| 2017/0049997 A1 | 2/2017 | Chao et al. |
| 2017/0095314 A1 * | 4/2017 | Baldwin .......... A61M 25/09041 |
| 2017/0112528 A1 | 4/2017 | Crisman et al. |
| 2017/0135908 A1 | 5/2017 | Tai et al. |
| 2017/0143349 A1 | 5/2017 | Raabe et al. |
| 2017/0151415 A1 | 6/2017 | Maeda et al. |
| 2017/0173302 A1 | 6/2017 | Beasley et al. |
| 2017/0182297 A1 | 6/2017 | Lysgaard et al. |
| 2017/0182304 A1 | 6/2017 | Bagwell et al. |
| 2017/0189059 A1 | 7/2017 | Long, Jr. et al. |
| 2017/0224967 A1 | 8/2017 | Gorn et al. |
| 2017/0232231 A1 | 8/2017 | Neoh et al. |
| 2017/0252560 A1 | 9/2017 | Imran |
| 2017/0296798 A1 * | 10/2017 | Kume .......... A61M 39/24 |
| 2017/0333149 A1 | 11/2017 | Stigall et al. |
| 2017/0333682 A1 | 11/2017 | Nardeo |
| 2017/0368238 A1 | 12/2017 | Robinson |
| 2018/0001063 A1 | 1/2018 | Aggerholm et al. |
| 2018/0008237 A1 | 1/2018 | Venkataraman et al. |
| 2018/0015277 A1 | 1/2018 | Stephens et al. |
| 2018/0036033 A1 | 2/2018 | Ignagni et al. |
| 2018/0093073 A1 | 4/2018 | Shimizu et al. |
| 2018/0117279 A1 | 5/2018 | Yachia et al. |
| 2018/0126129 A1 | 5/2018 | McDonough |
| 2018/0132821 A1 | 5/2018 | Dehghan Marvast et al. |
| 2018/0169383 A1 | 6/2018 | Khalaj et al. |
| 2018/0177980 A1 | 6/2018 | Khalaj et al. |
| 2018/0214288 A1 | 8/2018 | Smouse et al. |
| 2018/0221649 A1 | 8/2018 | Mulrooney et al. |
| 2018/0243046 A1 | 8/2018 | Scott et al. |
| 2018/0256849 A1 | 9/2018 | Linden et al. |
| 2018/0256907 A1 | 9/2018 | Katra et al. |
| 2018/0263595 A1 | 9/2018 | Goksel et al. |
| 2018/0272039 A1 | 9/2018 | Kim et al. |
| 2018/0289394 A1 * | 10/2018 | Shah .......... A61B 17/320016 |
| 2018/0296186 A1 | 10/2018 | Harks et al. |
| 2018/0296804 A1 * | 10/2018 | Bierman .......... A61M 39/0247 |
| 2018/0360494 A1 | 12/2018 | Melsheimer |
| 2019/0001031 A1 | 1/2019 | Real et al. |
| 2019/0015638 A1 | 1/2019 | Gruba et al. |
| 2019/0053790 A1 | 2/2019 | Grover et al. |
| 2019/0059857 A1 | 2/2019 | Ogura et al. |
| 2019/0076166 A1 | 3/2019 | Bierman et al. |
| 2019/0076167 A1 | 3/2019 | Fantuzzi et al. |
| 2019/0083061 A1 | 3/2019 | Choi |
| 2019/0091453 A1 | 3/2019 | Browne et al. |
| 2019/0091461 A1 | 3/2019 | Bonham et al. |
| 2019/0105466 A1 | 4/2019 | Schibli et al. |
| 2019/0105474 A1 | 4/2019 | Sheibley |
| 2019/0110795 A1 | 4/2019 | Koo et al. |
| 2019/0125318 A1 | 5/2019 | Sarna et al. |
| 2019/0125398 A1 | 5/2019 | Baldwin et al. |

FOREIGN PATENT DOCUMENTS

| | | | |
|---|---|---|---|
| CN | 206434630 U * | 8/2017 | |
| EP | 2296747 B1 * | 7/2015 | .......... A61B 1/0055 |
| JP | 4754626 B2 * | 8/2011 | .......... A61M 25/0009 |
| JP | 6301909 B2 * | 3/2018 | .......... A61M 25/0017 |
| WO | WO-9916499 A1 * | 4/1999 | .......... A61M 25/0662 |

(56) References Cited

FOREIGN PATENT DOCUMENTS

| WO | WO-2017053344 A1 * | 3/2017 | ............. | A61B 1/307 |
| WO | WO-2017180419 A1 * | 10/2017 | ............. | A61B 17/22 |

* cited by examiner

DEVICE SET DESIGNED FOR PCNL SURGERY

This application claims the benefit of Chinese Patent Application No. 201910783544.2, filed Aug. 23, 2019, the disclosure of which is incorporated herein by reference.

TECHNICAL FIELD

The present disclosure relates to the percutaneous nephrolithotomy (PCNL) surgery field, in particular, to a device set designed for PCNL surgery.

BACKGROUND

Percutaneous nephrolithotomy, commonly referred to as "drilling holes and removing stones," is a very effective method of removing and crushing kidney stones. Almost all kidney stones can be removed by percutaneous nephrolithotomy. Successful rate of renal pelvic stone removal is 96-98%, and successful rate of ureteral stone removal is 85%.

For PCNL surgery, there are two common ways to create a nephrostomy tract for removing calculi (i.e., a stone removal path). One way is using balloon dilation catheter to create a tract; and another way is using dilators to create a tract. Current products, especially a balloon dilation product, only includes part of required components. Thus, the physician needs to acquire several packages in order to get all required components, which is very inconvenient.

Moreover, this will also create waste in two aspects. Firstly, a total cost for several separate packages is higher than that for one package. Secondly, different packages will include the same components or extra (undesired) components, which will not be used during surgery (and it is not allowed to sterilize these components and reuse them). Physicians have to discard these components, which will also create waste.

For example, in the method of balloon dilation, physicians have to purchase a balloon dilation catheter set and a fascia dilation device set currently commercially available, in order to perform PCNL surgery with balloon dilation. A balloon dilation catheter kit includes a balloon dilation catheter, a sheath, a two-way valve and an inflation device. A fascia dilation device set includes a puncture needle, a guidewire, dilators of different sizes, a sheath and a drainage catheter. Only one sheath and normally one dilator are needed during a surgery for creating a tract with balloon dilation. The remaining unused new sheath and several unused new dilators have to be discarded after the surgery.

Another problem with existing percutaneous nephrolithotomy lies in that it is very difficult for a physician to insert a dilator/balloon at a right distance. In use, in order to create a uniform channel without causing any unwanted damage to a patient, such a component needs to be put in the right place within a tissue. However, when inserting various components, it is often difficult to ensure the same insertion depth. Too much insertion may cause unwanted injury to the patient; too less insertion may lead to incomplete expansion. This increases the difficulty of surgery.

SUMMARY

One aspect of the present disclosure is to provide a device set designed for percutaneous nephrolithotomy surgery, which set includes all necessary components to facilitate the physicians to use, and is advantageous in wastage and cost reduction.

A further aspect of the disclosure is that, with such a device set, the physician only needs to make sure that a first dilator is in the right place. The other dilators and balloon can follow the same insertion distance as the first dilator, which will greatly decrease the difficulty of surgery and increase the safety of surgery, thereby improving the reliability of surgery.

The present disclosure provides two kinds of device sets designed for PCNL surgery, respectively for the way of balloon catheter dilation and the way of dilator dilation. A device set designed for PCNL surgery using the way of balloon catheter dilation, comprising a puncture needle, a guidewire, a dilator, a balloon catheter, a sheath and a drainage catheter, can be called as a balloon catheter dilation device set. A device set designed for PCNL surgery using the way of dilator dilation, comprising a puncture needle, a guidewire, a plurality of dilators having different sizes, a sheath and a drainage catheter, can be called as a fascia dilation device set.

In either of the above two sets, all the included components can be placed in a single package. A plurality of compartments, for example in the form of recesses, are formed in the package, for accommodating stably the components to prevent the components from any damage caused by colliding with each other during handling.

For the balloon catheter dilation device set, the dilator has a tip length that is substantially the same as a tip length of the balloon catheter; for the fascia dilation device set, all the dilators have substantially the same tip length. Herein, a tip length of the dilator refers to a length of a distal cone portion of the dilator, and a tip length of the balloon catheter refers to a length of a portion between a distal tip of the balloon catheter and a shoulder of a distal cone of the balloon catheter.

By arranging such that the tip lengths are substantially the same, the above-mentioned another problem can be solved, and the above-mentioned another object of the present disclosure can be achieved. The above-mentioned problem arises because, in the existing products, the tips of the dilator and the balloon catheter have different lengths, while the tip portions are non-effective for the dilation of the channel (these portions can be called as a non-effective portion). In use, the insertion of various components often results in inconsistent insertion due to the presence of the tips.

The tip length may be in a range of 0.8 cm to 3 cm, for example 1.2 cm or 2 cm.

In either of the above two device sets, one or more of the puncture needle, guidewire, dilator, balloon catheter, sheath and drainage catheter are provided with scaler markers.

In the above balloon catheter dilation device set, the sheath has a size matched with a size of the balloon catheter; a size of the drainage catheter is 2 Fr less than a size of the balloon catheter.

The balloon catheter dilation device set may further comprise a drainage bag, an inflation device, a stopcock, and/or a securement device. Preferably, the drainage bag may have a volume in a range of 500 ml to 3000 ml.

The above balloon catheter dilation device set may be sized to be 12 Fr, 14 Fr, 16 Fr, 18 Fr, 20 Fr, 22 Fr, 24 Fr, 26 Fr, 28 Fr, 30 Fr, or 32 Fr.

In the above fascia dilation device set, the sheath has a size matched with a size of the dilator having the largest size; a size of the drainage catheter is 2 Fr less than a size of the dilator having the largest size.

The above fascia dilation device set may further comprise a drainage bag and/or a securement device. The drainage bag has a volume in a range of 500 ml to 3000 ml.

The above fascia dilation device set may be sized to be 8 Fr, 10 Fr, 12 Fr, 14 Fr, 16 Fr, 18 Fr, 20 Fr, 22 Fr, 24 Fr, 26 Fr, 28 Fr, 30 Fr, or 32 Fr.

In either of the above two device sets, the sheath may be a common sheath or a tearable sheath.

Other objects, features, and details of the present disclosure can be more fully understood with reference to the following detailed description of exemplary embodiments in conjunction with the accompanying drawings and according to the appended claims. A person skilled in the art will understand advantages of corresponding embodiments and various additional embodiments by reading the following detailed description of the corresponding embodiments with reference to the drawings as listed below. In addition, features in the drawings discussed below are not necessarily drawn to scale. Sizes of the features and elements in the drawings may be appropriately enlarged or reduced to more clearly illustrate the embodiments of the present disclosure.

BRIEF DESCRIPTION OF THE DRAWINGS

The present disclosure is further described as below with reference to the accompanying drawings and embodiments, wherein like reference numerals refer to like elements.

DETAILED DESCRIPTION

Various illustrative embodiments of the present disclosure are described below. In this description, for the sake of explanation only, various systems, structures and devices are schematically depicted in the drawings, but all the features of actual systems, structures and devices are not described. For example, well-known functions or structures are not described in detail to avoid unnecessary details to obscure the present disclosure. Of course, it should be understood that in any practical application, many specific implementation decisions need to be made to achieve the specific goals of the developer or user, and the system-related and industry-related restrictions need to be observed. These specific goals may vary with actual applications. In addition, it should be understood that although such specific implementation decisions are complicated and time-consuming, this is a routine task for those of ordinary skill in the art who benefit from the present application.

The terms and phrases used herein should be understood and interpreted as having a meaning consistent with the understanding of those terms and phrases by those skilled in the relevant art. The consistent usage of terms or phrases herein is not intended to imply a specific definition of the term or phrase, that is, a definition that differs from the ordinary and customary meanings understood by those skilled in the art. For terms or phrases intended to have a special meaning, that is, meanings different from those understood by the skilled person, this special meanings will be clearly listed in the description by definition, giving special meanings to the term or phrase directly and unambiguously.

Unless the content requires, throughout the following description and claims, the words "comprising" and its variations, such as "including", will be interpreted in an open and inclusive sense, that is, as "comprising but not limited to".

In the present disclosure, the terms "first", "second", and the like are used for descriptive purposes only and cannot be construed as indicating relative importance or indicating the number of technical features. Thus, features defined as "first", "second", or the like may explicitly or implicitly include one or more of the features. In the description of the present disclosure, the meaning of "a plurality of" is two or more, unless otherwise specified.

In the present disclosure, unless otherwise clearly specified and defined, such terms as "mounted", "connected", "coupled", "fixed", and so on should be understood in a broad sense. For example, it can be a fixed connection, or a detachable connection, or an integral connection; it can be a mechanical connection or an electrical connection; it can be directly connected or be indirectly connected via an intermediate medium; or it can be an internal communication between two components. Those of ordinary skill in the art can understand the specific meanings of the above terms in the present disclosure according to specific situations.

In the present disclosure, for convenience of description, the operator (for example, a physician) is used as a reference object, and the side close to the operator is called "proximal", and the side away from the operator is called "distal".

First Embodiment

Figure 1:
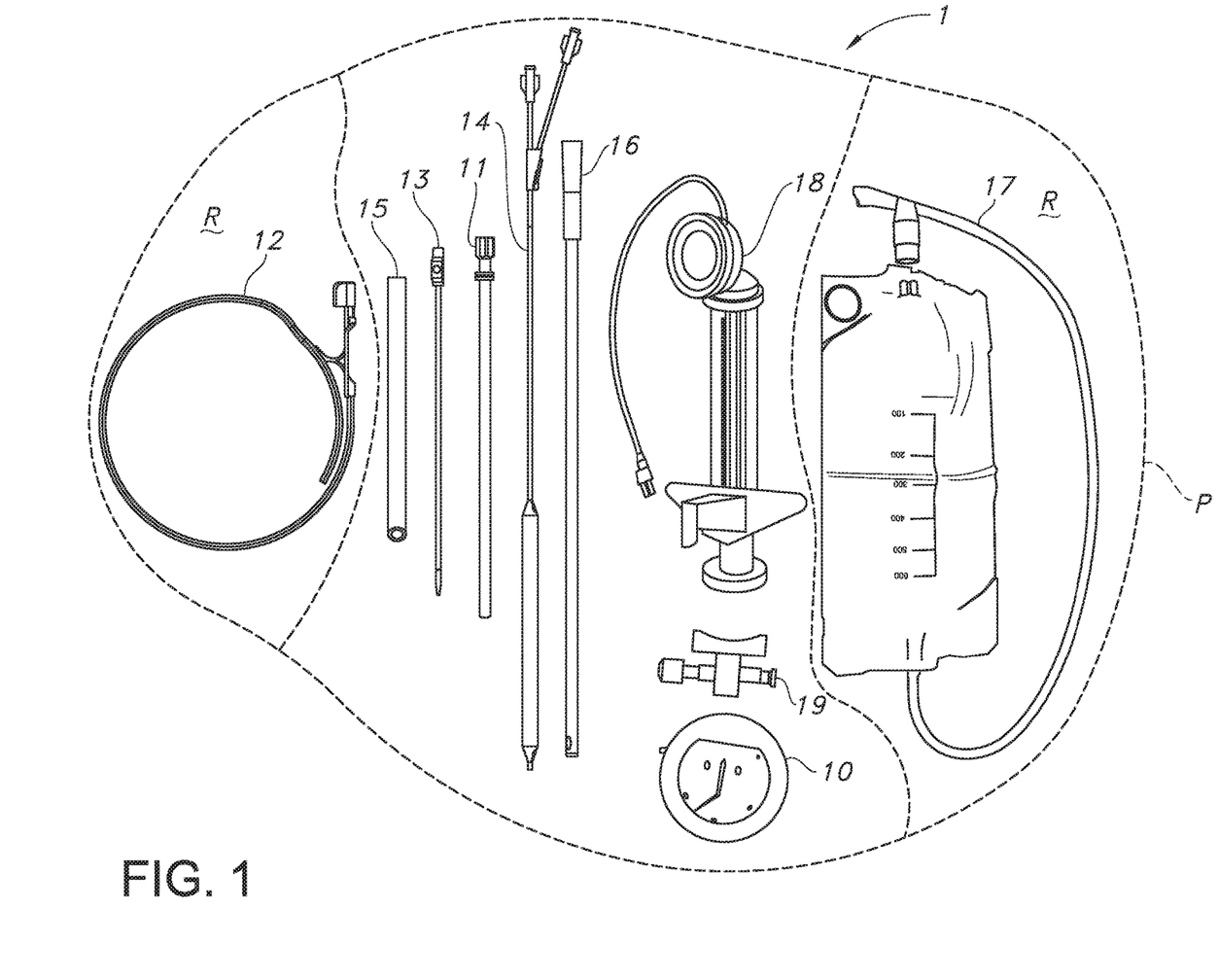
FIG. 1 is an overall schematic view of a balloon catheter dilation device set designed for percutaneous nephrolithotomy surgery according to a first embodiment of the present disclosure.

Referring to FIG. 1, the first embodiment according to the present disclosure provides a balloon catheter dilator device set 1 designed for the percutaneous nephrolithotomy surgery.

The balloon catheter dilator set 1 includes or consists of the following components:
a) 1 pcs 18 G puncture needle 11;
b) 1 pcs 0.035" or 0.038" guidewire 12;
c) 1 pcs 8 Fr dilator or 1 pcs 10 Fr dilator (only an 8 Fr dilator 13 is shown in the figure);
d) 1 pcs balloon catheter 14 having a size the same as a set size of the device set;
e) 1 pcs sheath 15 adapted to match with the size of the balloon catheter 14;
f) 1 pcs drainage catheter 16 having a size that is 2 Fr less than the size of the balloon catheter 14;
g) 1 pcs drainage bag 17 having a volume in a range of 500 ml to 3000 ml;
h) 1 pcs inflation device 18;
i) 1 pcs stopcock 19; and
j) 1 pcs securement device 10.

The set size of the balloon catheter dilation device set 1 may include 12 Fr, 14 Fr, 16 Fr, 18 Fr, 20 Fr, 22 Fr, 24 Fr, 26 Fr, 28 Fr, 30 Fr, or 32 Fr. The set size thereof is an inner diameter of a desired nephrostomy tract (i.e., a stone removal path) that is finally completed.

The balloon catheter 14 has the same specification or nominal size as the set size. For example, as shown in FIG. 1, the balloon catheter dilator device set 1 may have a set size of 24 Fr, in which case it may be referred to as a 24 Fr balloon catheter dilator device set. In the 24 Fr balloon catheter dilator device set, the specification or nominal size of the balloon catheter 14 is 24 Fr, the size of the sheath 15 is 24 Fr, and the size of the drainage catheter 16 is 22 Fr; and the dilator may be selected to be an 8 Fr dilator (as shown in FIG. 1) or a 10 Fr dilator. Physicians can select to use the balloon catheter dilator device sets of different sizes according to patients, conditions, etc.

The device set may include all of the above components, or some of the above components.

The components included in the device set can be placed in a single package P. A plurality of compartments, for example in the form of recesses R, are formed in the package, and can be configured for accommodating stably various components to prevent the components from any damage caused by colliding with each other during handling.

Except for the stopcock and the securement device, all the other components may be provided with scale markers, so as to facilitate the physician to get to know the usage status of the components at any time during use, such as insertion depth, filled volume, inflation pressure, etc.

The sheath may be a common sheath or a tearable sheath.

Figure 2:
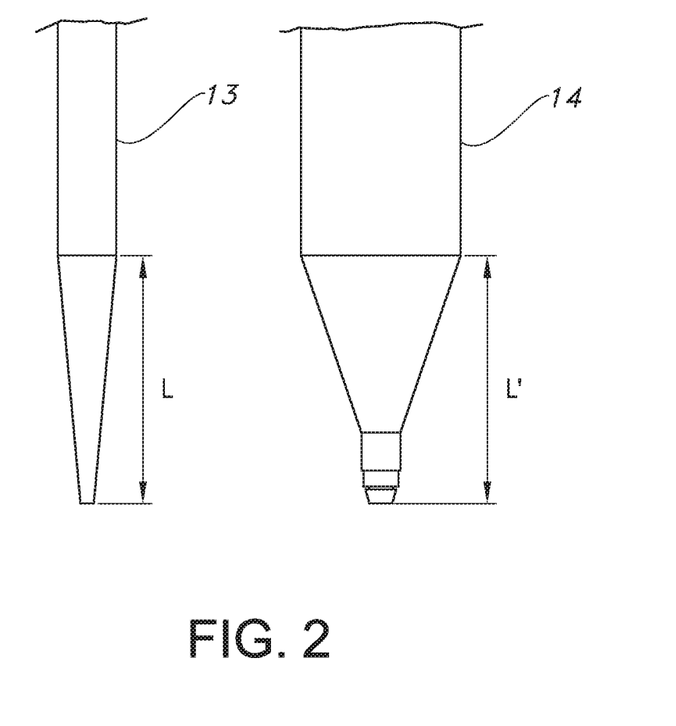
FIG. 2 is a schematic view of tips of the balloon catheter and of the dilator as shown in FIG. 1 according to the first embodiment of the present disclosure.

In particular, in the balloon catheter dilation device set 1, the tip length L of the dilator 13 is substantially the same as the distal tip length L' of the balloon catheter 14. Herein, as shown in FIG. 2, a tip length of the dilator 13 refers to a length of a distal cone portion of the dilator, and a tip length of the balloon catheter 14 refers to a length of a portion between a distal tip of the balloon catheter and a shoulder of a distal cone of the balloon catheter. The tip length L and L' may be in a range of 0.8 cm to 3 cm, for example 1.2 cm or 2 cm. The tip length L of the dilator and the tip length L' of the balloon catheter have a difference less than 4 mm, and can be regarded as being substantially the same length.

During surgery, physician can insert a puncture needle 11 as guided with x-ray and/or ultrasound fluoroscopy. After positioning the puncture needle in place, the physician can record its insertion depth. Then, as guided by the guidewire 12 and with the assistance of scale markers, for example, an 8 Fr dilator or a 10 Fr dilator is inserted, with a dilator insertion depth equal to the puncture needle's insertion depth plus the tip length (for example, the tip length is 1.2 cm). The insertion depth of the subsequently inserted balloon catheter 14 is the same as the insertion depth of the dilator 13.

This device set solves the aforementioned technical problems. In particular, physicians do not need to purchase several packages in order to get all required components, but only need to purchase one set to get ready for all the necessary components, which is very convenient for physicians. Moreover, all the components in the device set are needed during surgery, which will not cause wastage.

In addition, the tips of the dilator and of the balloon catheter in the device set of the present disclosure are designed to have substantially the same length, such that the physicians can easily insert the balloon catheter at the correct distance during use. This greatly reduces the difficulty of surgery, avoids undesirable injuries to the patient, and can ensure the reliability and safety of surgery.

Second Embodiment

Figure 3:
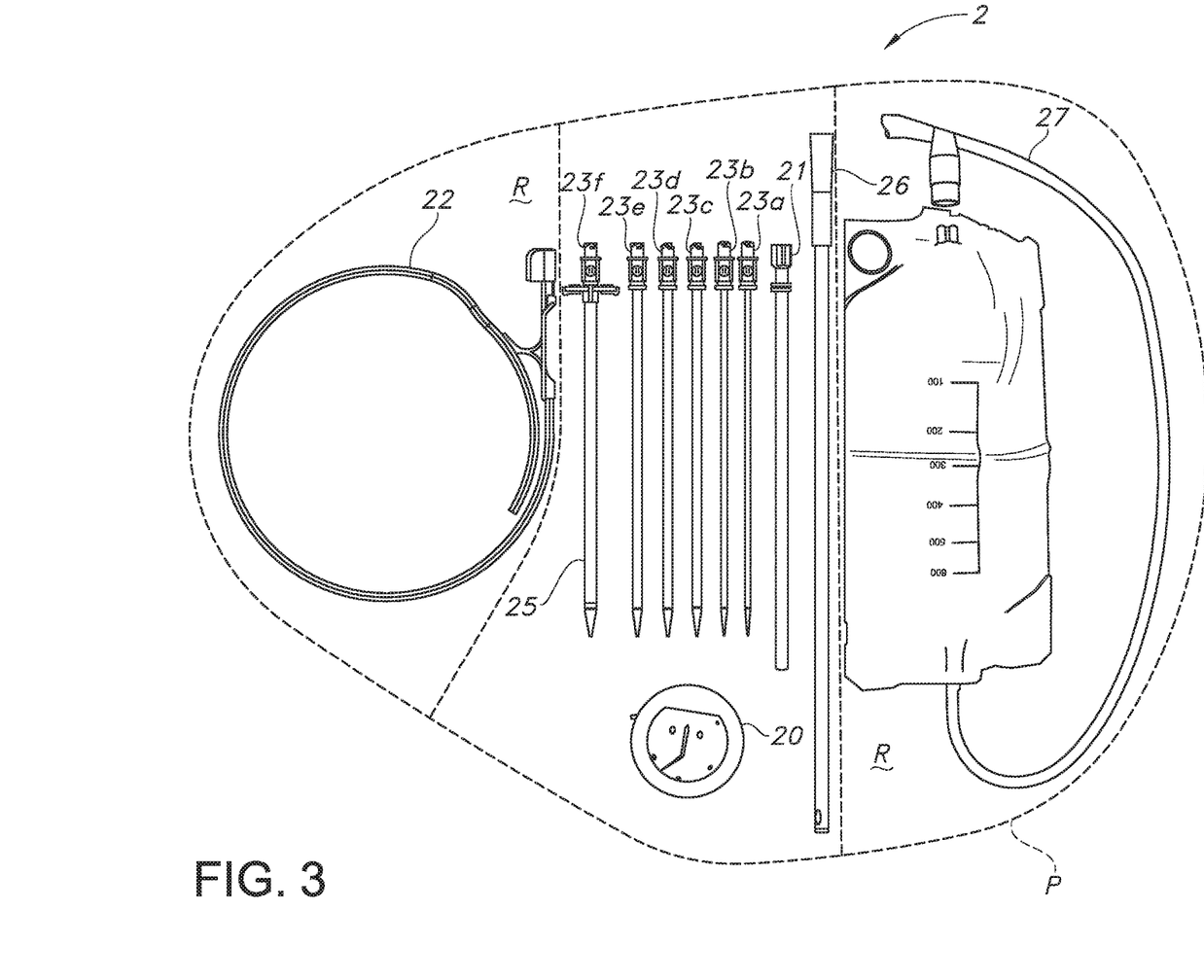
FIG. 3 is an overall schematic view of a fascia dilation device set designed for percutaneous nephrolithotomy surgery according to a second embodiment of the present disclosure.

Referring to FIG. 3, the second embodiment according to the present disclosure provides a fascia dilation device set 2 designed for the percutaneous nephrolithotomy surgery.

The fascia dilation device set 2 includes or consists of the following components:
a) 1 pcs 18 G puncture needle 21;
b) 1 pcs 0.035" or 0.038" guidewire 22;
c) a plurality of dilators 23a-23f having different sizes, the dilators having a number and sizes dependent on the set size of the device set;
d) 1 pcs tearable sheath 25 having a size matched with a dilator 23f having the largest size;
e) 1 pcs drainage catheter 26 having a size 2 Fr less than the dilator 23f having the largest size;
f) 1 pcs drainage bag 27 having a volume in a range of 500 ml to 3000 ml; and
g) 1 pcs securement device 20.

The set size of the fascia dilation device set 2 may include 8 Fr, 10 Fr, 12 Fr, 14 Fr, 16 Fr, 18 Fr, 20 Fr, 22 Fr, 24 Fr, 26 Fr, 28 Fr, 30 Fr, or 32 Fr. The set size thereof is an inner diameter of a desired nephrostomy tract (i.e., a stone removal path) that is finally completed. The size of the dilator 23f having the largest size is the same as the set size of the device set. For example, as shown in FIG. 3, the fascia dilation device set 2 may have a set size of 18 Fr, in which case it may be referred to as an 18 Fr fascia dilation device set. Herein, the size of the dilator 23f having the largest size is 18 Fr, the size of the sheath 25 is 18 Fr, and the size of the drainage catheter 26 is 16 Fr; and the sizes of the other dilators 23a to 23e are 8 Fr, 10 Fr, 12 Fr, 14 Fr, 16 Fr in order (in the embodiment shown in FIG. 3, there are six dilators in total, in which the largest size dilator 23f is nested in the sheath 25). Physicians can select to use various balloon catheter dilator device sets of different set sizes according to different patients, different conditions, etc.

The device set may include all of the above components, or some of the above components.

Similar to the first embodiment, the components included in the device set according to the second embodiment can be placed in a single package P. A plurality of compartments, for example in the form of recesses R, are formed in the package, and can be configured for accommodating stably various components to prevent the components from any damage caused by colliding with each other during handling.

Except for the guidewire and the securement device, all the other components may be provided with scale markers, so as to facilitate the physician to get to know the usage status of the components at any time during use, such as insertion depth, filled volume, inflation pressure, etc.

In this embodiment, the sheath is shown to be a tearable sheath. Of course, a non-tearable common sheath may also be used.

Figure 4:
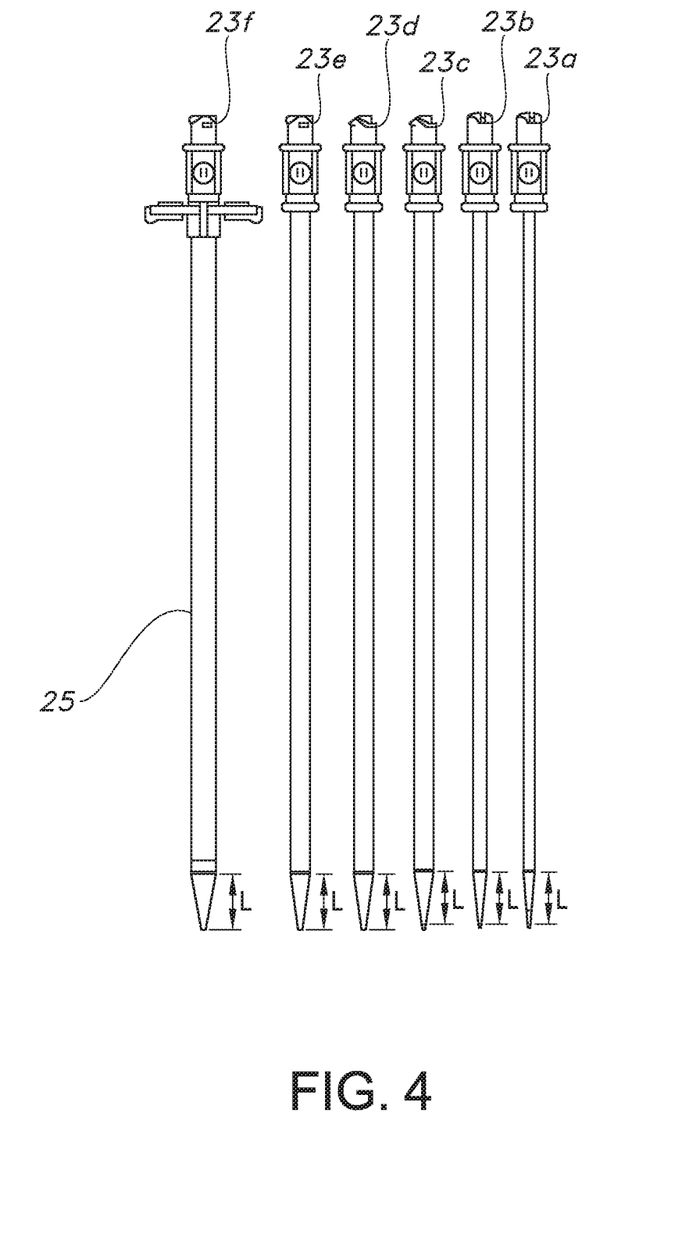
FIG. 4 is a schematic view of a tip of the dilator as shown in FIG. 3 according to the second embodiment of the present disclosure.

In particular, in the fascia dilation device set, the tip lengths L of all the dilators 23a to 23f are substantially the same, as shown in FIG. 4. Herein, a tip length L of the dilator refers to a length of a distal cone portion of the dilator. The tip length L may be in a range of 0.8 cm to 3 cm, for example 2 cm. The tip lengths of different dilators have a difference less than 4 mm, and can be regarded as being substantially the same length.

During surgery, physician can insert a puncture needle 21 as guided with x-ray and/or ultrasound fluoroscopy. After positioning the puncture needle 21 in place, the physician can record its insertion depth. Then, as guided by the guidewire 22 and with the assistance of scale markers, the dilators 23a to 23f are inserted in ascending order, with the insertion depth equal to the puncture needle 21's insertion depth plus the tip length (for example, the tip length is 2 cm).

Like the first embodiment, the device set according to the second embodiment solves the aforementioned technical problems existing in the prior art and produces advantageous technical effects, which will not be repeated here.

The present disclosure may include any feature or combination of features implicitly or explicitly disclosed herein or a generic concept thereof, and is not limited to any defined scope as listed above. Any elements, features and/or structural arrangements described herein may be combined in any suitable manner.

The specific embodiments disclosed above are merely exemplary, and it will be apparent to those skilled in the art who benefit from the teachings herein that the present disclosure can be modified and implemented in different but equivalent manners. For example, steps of the above-mentioned method can be performed in a different order. Further, the details of construction or design shown herein are not limited except those as set forth in the following claims. It is therefore obvious that changes and modifications can be made to the specific embodiments as disclosed above, and all these variations are considered to fall within the scope and spirit of the present disclosure. Therefore, the protection sought herein is set forth in the appended claims.

What is claimed is:

1. A device set designed for PCNL surgery, comprising, in a single package:
    a puncture needle,
    a guidewire,
    a dilator including a dilator cone on a distal end of the dilator,
    a balloon catheter including a balloon catheter cone at a distal portion of the balloon catheter,
    a sheath, and
    a drainage catheter,
    wherein a tip length of the dilator between a proximal end of the dilator cone and a distal end of the dilator cone is the same as a tip length of the balloon catheter between a proximal end of the balloon catheter cone and a distal end of the balloon catheter.

2. The device set according to claim 1, wherein the tip length is in a range of 0.8 cm to 3 cm.

3. The device set according to claim 2, wherein the tip length is 1.2 cm.

4. The device set according to claim 1, wherein a plurality of chambers are formed in the package.

5. The device set according to claim 1, wherein one or more of the puncture needle, the guidewire, the dilator, the balloon catheter, the sheath and the drainage catheter are provided with scale markers.

6. The device set according to claim 1, wherein the sheath has a size corresponding to a size of the balloon catheter.

7. The device set according to claim 1, wherein the sheath of the device set is a tearable sheath.

8. The device set according to claim 1, wherein a size of the drainage catheter is 2 Fr less than a size of the balloon catheter.

9. The device set according to claim 1, further comprising one or more of the following: a drainage bag, an inflator, and a stopcock.

10. The device set according to claim 1, wherein the device set further comprises a drainage bag having a volume in a range of 500 ml to 3000 ml.

* * * * *